US00PP18965P2

(12) United States Plant Patent
van Veen

(10) Patent No.: US PP18,965 P2
(45) Date of Patent: Jun. 24, 2008

(54) ***ASTILBE* PLANT NAMED 'VISION IN WHITE'**

(50) Latin Name: *Astilbe chinensis*
Varietal Denomination: Vision in White

(75) Inventor: Johannes Gerardus van Veen, Noorden (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/725,803

(22) Filed: Mar. 20, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—C. A. Whealy

(57) ABSTRACT

A new and distinct cultivar of *Astilbe* plant named 'Vision in White', characterized by its upright and sturdy plant habit; strong and healthy foliage; freely and uniformly flowering habit; white-colored flowers; and good garden performance.

3 Drawing Sheets

Botanical designation: *Astilbe chinensis.*
Cultivar denomination: 'Vision in White'.

BACKGROUND OF THE INVENTION

The present invention relates to a new and distinct cultivar of *Astilbe,* botanically known as *Astilbe chinensis* and hereinafter referred to by the name 'Vision in White'.

The new *Astilbe* is a product of a planned breeding program conducted by the Inventor in Noorden, The Netherlands. The objective of the breeding program was to create new vigorous *Astilbe* cultivars with healthy foliage and attractive flower coloration.

The new *Astilbe* originated from a cross-pollination made by the Inventor in 2003 in Noorden, The Netherlands, of the *Astilbe chinensis* cultivar Vision, not patented, as the female, or seed, parent with the *Astilbe chinensis* cultivar D üsseldorf, not patented, as the male, or pollen, parent. The new *Astilbe* was discovered and selected by the Inventor as a single flowering plant within the progeny of the stated cross-pollination in a controlled environment in Noorden, The Netherlands in 2005.

Asexual reproduction of the new *Astilbe* by divisions in a controlled environment in Noorden, The Netherlands since 2005, has shown that the unique features of this new *Astilbe* are stable and reproduced true to type in successive generations.

SUMMARY OF THE INVENTION

The cultivar Vision in White has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Vision in White'. These characteristics in combination distinguish 'Vision in White' as a new and distinct cultivar of *Astilbe:*

1. Upright and sturdy plant habit.
2. Strong and healthy foliage.

3. Freely and uniformly flowering habit.
4. White-colored flowers.
5. Good garden performance.

Plants of the new *Astilbe* and the parents differ primarily in flower coloration as plants of the cultivar Vision have light pink-colored flowers and plants of the cultivar D üsseldorf have pink-colored flowers.

Plants of the new *Astilbe* can be compared to plants of the cultivar Deutschland, not patented. In side-by-side comparisons conducted in Noorden, The Netherlands, plants of the new *Astilbe* and the cultivar Deutschland differed in the following characteristics:

1. Plants of the new *Astilbe* were more vigorous than plants of the cultivar Deutschland.
2. Plants of the new *Astilbe* had healthier and more attractive foliage than plants of the cultivar Deutschland.
3. Inflorescences of plants of the new *Astilbe* were positioned above the foliage whereas inflorescences of plants of the cultivar Deutschland were positioned above and within the foliage.

BRIEF DESCRIPTION OF THE PHOTOGRAPHS

The accompanying colored photographs illustrate the overall appearance of the new *Astilbe,* showing the colors as true as it is reasonably possible to obtain in colored reproductions of this type. Colors in the photographs may differ slightly from the color values cited in the detailed botanical description which accurately describe the colors of the new *Astilbe.*

The photograph on the first sheet comprises a side perspective view of a typical flowering plant of 'Vision in White' grown in an outdoor nursery.

The photograph on the second sheet is a close-up view of a typical inflorescence of 'Vision in White'.

The photograph at the top of the third sheet is a close-up view of typical flowers of 'Vision in White'.

The photograph at the bottom of the third sheet is a close-up view of the upper surface of a typical leaf of 'Vision in White'.

DETAILED BOTANICAL DESCRIPTION

The aforementioned photographs and following observations, measurements and values describe plants grown in containers in Noorden, The Netherlands, under commercial practice in during the early autumn in an outdoor nursery with day temperatures ranging from 14° C. to 35° C. and night temperatures ranging from 10° C. to 18° C. Plants had been growing for about one year when the photographs and description were taken. In the following description, color references are made to The Royal Horticultural Society Colour Chart, 2001 Edition, except where general terms of ordinary dictionary significance are used.

Botanical classification: *Astilbe chinensis* cultivar Vision in White.

Parentage:

*Female, or seed, parent.*—*Astilbe chinensis* cultivar Vision, not patented.

*Male, or pollen, parent.*—*Astilbe chinensis* cultivar Düsseldorf, not patented.

Propagation:

*Type.*—By divisions.

*Time to produce a rooted plant.*—About two months at 18° C. to 20° C.

*Root description.*—Fine; brown in color.

*Rooting habit.*—Freely branching; moderately dense.

Plant description:

*Plant form/habit.*—Herbaceous perennial. Upright and sturdy plant habit; roughly triangular. Flowering stems and leaves basal; dense and bushy growth habit; moderately vigorous growth habit. Freely and uniformly flowering with numerous flowers on branched panicles.

*Growth rate.*—Moderate to fast; from divisions, about 20 weeks are required to produce fully-grown flowering plants.

*Plant height* (*soil level to top of foliar plane*).—About 35 cm.

*Plant height* (*soil level to top of inflorescences*).—About 61 cm.

*Plant width* (*spread*).—About 48.5 cm.

*Stem description.*—Length: About 29 cm. Diameter: About 4 mm. Internode length: About 11.2 cm. Strength: Strong. Texture: Sparsely pubescent. Color: 144A.

Foliage description:

*Arrangement.*—Alternate; biternately compound.

*Leaf length* (*excluding petiole*).—About 25.6 cm.

*Leaf width.*—About 20.7 cm.

*Lateral leaflet length.*—About 7.1 cm.

*Lateral leaflet width.*—About 3.5 cm.

*Terminal leaflet length.*—About 9.5 cm.

*Terminal leaflet width.*—About 5.9 cm.

*Lateral and terminal leaflet shape.*—Ovate to elliptic.

*Lateral and terminal leaflet apex.*—Acute.

*Lateral and terminal leaflet base.*—Attenuate.

*Lateral and terminal leaflet margin.*—Biserrate.

*Lateral and terminal leaflet texture, upper and lower surfaces.*—Sparsely pubescent; slightly rough.

*Lateral and terminal leaflet venation pattern.*—Pinnate.

*Lateral and terminal leaflet color.*—Developing leaves, upper and lower surfaces: 144B; at the margin (about 0.3 mm wide), flushed with 178B. Fully expanded leaves, upper surface: Darker than 139A; venation, 138A. Fully expanded leaves, lower surface: 137B to 137C; venation, 147B to 147C.

*Leaf petiole length.*—About 16.2 cm.

*Leaf petiole diameter.*—About 4 mm.

*Leaflet petiole length.*—About 4.6 cm.

*Leaflet petiole width.*—About 4 mm.

*Leaf and leaflet petiole texture, upper and lower surfaces.*—Smooth, glabrous.

*Leaf and leaflet petiole color, upper and lower surfaces.*—144A; towards the base, 144B to 144C; at the nodes, 183B to 183C.

Flower description:

*Flower type/habit.*—Numerous single rotate flowers arrange on branched panicles; flowers fact upright, outward or downward depending on position on the panicle. Panicles conical in shape. Freely and uniformly flowering habit with about 1,250 flower buds and flowers developing per inflorescence.

*Fragrance.*—Moderately fragrant; sweet.

*Natural flowering season.*—Continuously flowering during the summer and late summer in Noorden, The Netherlands.

*Postproduction longevity.*—Flowers last about ten days on the plant. Flowers persistent.

*Flower buds.*—Height: About 3 mm. Diameter: About 2 mm. Shape: Ovoid. Color: 157C to 157D; calyx, 145C to 145D.

*Inflorescence height.*—About 32 cm.

*Inflorescence diameter.*—About 18.6 cm.

*Flower diameter.*—About 6 mm.

*Flower depth.*—About 7 mm.

*Petals.*—Quantity per flower: Typically five in a single whorl. Length: About 6 mm. Lobe width: About 1.5 mm. Shape: Narrowly oblanceolate. Apex: Broadly acute to obtuse. Margin: Entire. Texture, upper and lower surfaces: Smooth, glabrous. Color: Developing petals, upper and lower surfaces: Close to 155D. Fully expanded petals, upper and lower surfaces: Close to 155D.

*Sepals.*—Quantity per flower: Typically five in a single whorl, fused towards the base; campanulate calyx. Length: About 2.5 mm. Width: About 1.5 mm. Shape: Ovate. Apex: Acute. Margin: Entire. Texture, upper and lower surfaces: Smooth, glabrous. Color, developing sepals, upper and lower surfaces: Between 145C to 145D and 158D. Color, fully expanded sepals, upper and lower surfaces: 155A.

*Peduncles.*—Length: About 29 cm. Diameter: About 4 mm. Angle: Erect; secondary flowering stems, about 67.5° C. from vertical. Strength: Strong. Texture: Smooth, glabrous. Color: 144A.

*Pedicels.*—Length: About 0.75 mm. Diameter: About 0.5 mm. Angle: About 45° from vertical. Strength: Moderately strong. Texture: Smooth, glabrous. Color: 150C to 150D.

*Reproductive organs.*—Stamens: Quantity per flower: Typically ten; anthers basifixed. Filament length: About 3.5 mm. Anther shape: Oblong. Anther length: About 0.2 mm. Anther color: 157D. Pollen amount: Scarce. Pollen color: 155D. Pistils: Quantity per flower: Two. Pistil length: About 1 mm. Stigma shape: Club-shaped. Stigma color: 155A. Style length: About 0.9 mm. Style color: 155A. Ovary color: 158D.

*Seed/fruit.*—Seed and fruit development have not been observed.

Disease/pest resistance: Plants of the new *Astilbe* have not been noted to be resistant to pathogens and pests common to *Astilbe*.

Garden performance: Plants of the new *Astilbe* have been observed to have good garden performance and tolerate rain, wind and high temperatures of about 35° C. Plants of the new *Astilbe* have been observed to be hardy to USDA Zone 5.

It is claimed:

1. A new and distinct *Astilbe* plant named 'Vision in White' as illustrated and described.

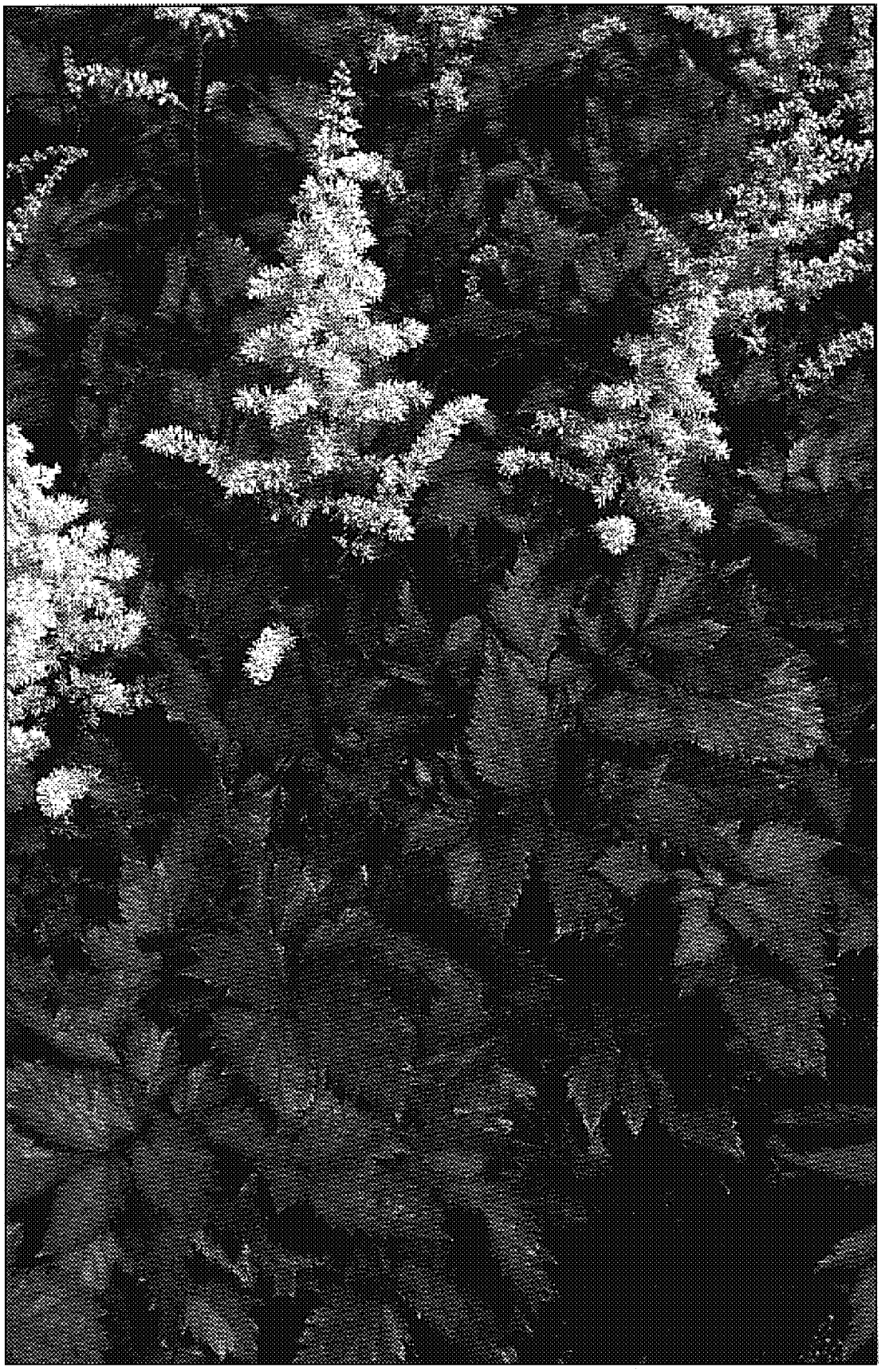

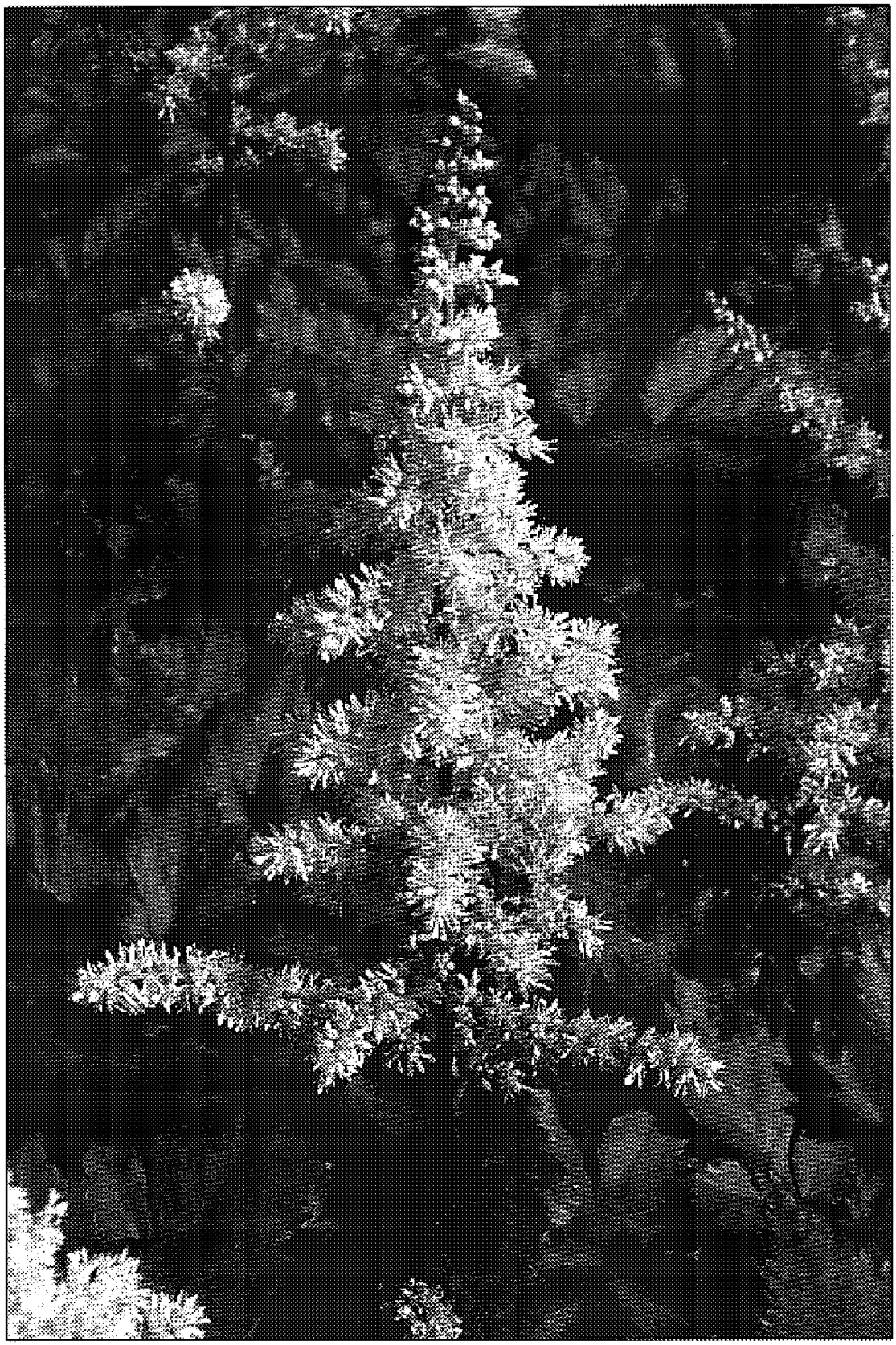

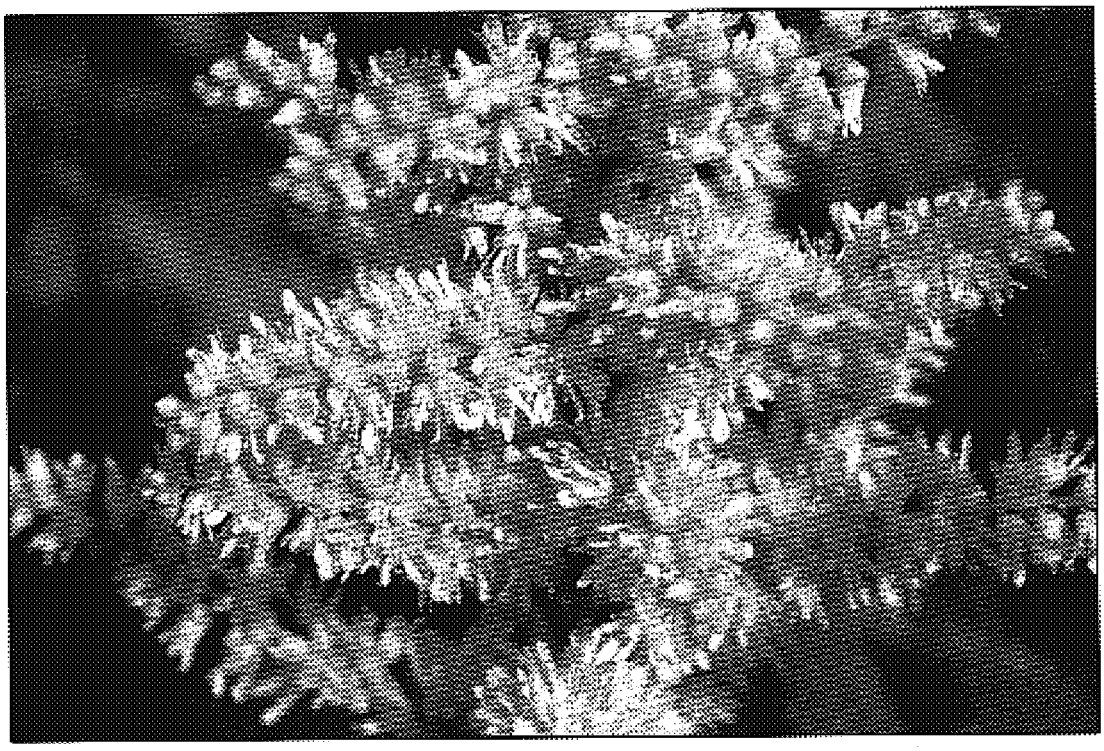
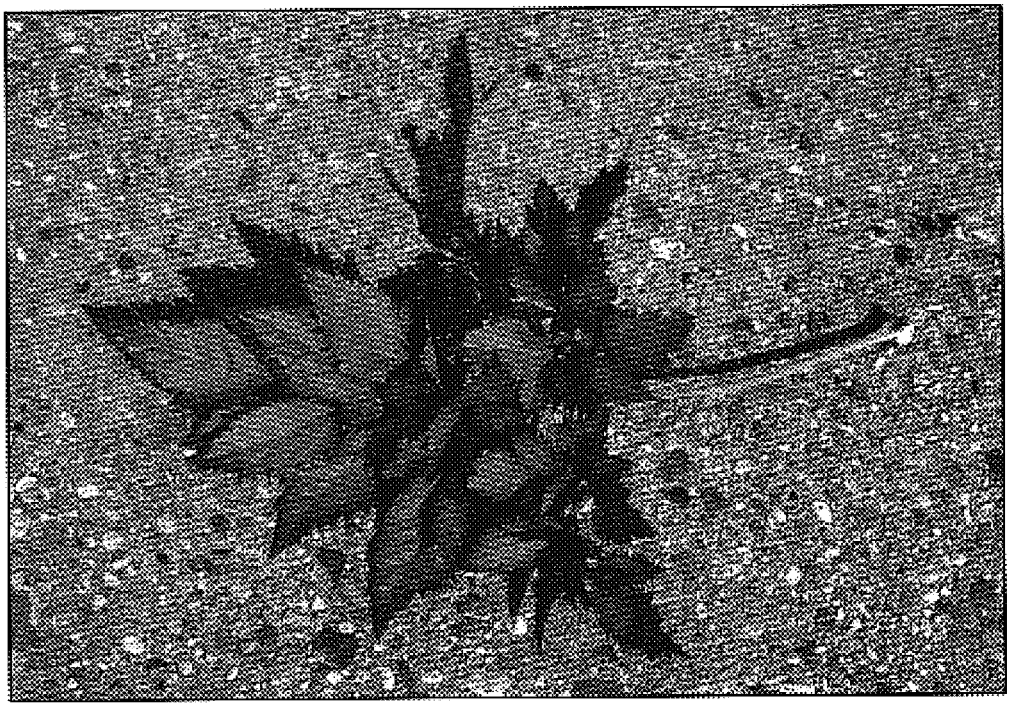

* * * * *